(12) United States Patent
U'ren et al.

(10) Patent No.: US 6,319,671 B1
(45) Date of Patent: Nov. 20, 2001

(54) COMPOSITIONS AND METHODS FOR DETERMINING PREDISPOSITION TO INSULIN DEPENDENT DIABETES MELLITUS

(75) Inventors: Jack U'ren, Kirkland; Sharon Howard, Seattle; Vivian H. Gersuk, Bellevue, all of WA (US)

(73) Assignee: Saigene Corporation, Seattle, WA (US)

( * ) Notice: Subject to any disclaimer, the term of this patent is extended or adjusted under 35 U.S.C. 154(b) by 0 days.

(21) Appl. No.: 09/367,905

(22) PCT Filed: Feb. 19, 1998

(86) PCT No.: PCT/US98/03089

§ 371 Date: Dec. 13, 2000

§ 102(e) Date: Dec. 13, 2000

(87) PCT Pub. No.: WO98/37237

PCT Pub. Date: Aug. 27, 1998

Related U.S. Application Data

(60) Provisional application No. 60/038,246, filed on Feb. 21, 1997.

(51) Int. Cl.[7] .............................. C12Q 1/68; C12P 19/34
(52) U.S. Cl. ............................................... 435/6; 435/91.2
(58) Field of Search ....................... 435/6, 91.2; 536/22.1

(56) References Cited

U.S. PATENT DOCUMENTS 5,908,749 * 6/1999 Mignot et al. ............................ 435/6
5,972,604 * 10/1999 Santamaria et al. ..................... 435/6
6,204,245 * 3/2001 Siegel et al. ........................... 514/11

* cited by examiner

*Primary Examiner*—Eggerton A. Campbell
(74) *Attorney, Agent, or Firm*—Townsend and Townsend and Crew LLP

(57) ABSTRACT

Methods for detecting in a human biological sample the presence of HLA DQB1 alleles 0201/0202, 0302/0303, and/or 0602 which are associated with increased or decreased susceptibility to insulin dependent diabetes mellitus.

16 Claims, No Drawings

COMPOSITIONS AND METHODS FOR DETERMINING PREDISPOSITION TO INSULIN DEPENDENT DIABETES MELLITUS

CROSS REFERENCE TO RELATED APPLICATION

This application a 371 of PCT/US98/03089, filed on Feb. 19, 1998 is a continuation-in-part of U.S. provisional application Ser. No. 60/038,246 (U'ren et al.) filed Feb. 21, 1997.

ACKNOWLEDGEMENT

This invention was made with United States Government support under Grant No. 2R44DK45547-02, awarded by the National Institutes of Health. The United States Government has certain rights in this invention.

FIELD OF THE INVENTION

The present invention is directed to methods for selective and simultaneous hybridization of multiple allele-specific probes to the HLA DQB1 locus. Simultaneous detection of the HLA alleles allows more rapid screening than sequential assay methods. The HLA DQB1 alleles detected by the present invention are associated with susceptibility to, or protection from, insulin dependent diabetes mellitus.

BACKGROUND OF THE INVENTION

The HLA class II gene cluster plays an essential role in immune activation by presenting processed antigens to various lymphoid cell types of the immune system. This role is not only functional during the body's normal defense against invading pathogens, but also during an inappropriate attack on self tissues causing autoimmune diseases. In type I diabetes (IDDM or insulin dependent diabetes mellitus) this autoimmune attack is on the islet cells of the pancreas whose function is to secrete insulin and regulate the body's glucose metabolism. Not all of the hundreds of possible HLA genes are associated with this inappropriate autoimmune attack. Indeed, only two of the 25 known HLA DQB1 genes, namely DQB1 0201 and 0302, are highly associated with the disease in caucasian populations while the DQB1 0303 allele is associated with increased risk for IDDM in the Asian population. In addition, another of these genes, DQB1 0602, has the ability to suppress this greater risk of contracting diabetes when present as part of the heterozygote inheritance with 0302. The rarer DQB1 0202 allele has not been studied with respect to diabetes risk assessment. However, since its DNA sequence is identical to the DQB1 0201 sequence in the region of antigen binding, it is thought to impart the same increased risk as the DQB1 0201 allele. The increased risk of contracting type I diabetes can be as high as 200 fold for people who have inherited both the DQB1 0201 and 0302 genes (see, J. Nepom, *Diabetic Reviews* 1:93 (1993)).

U.S. Pat. No. 5,039,606 "Diagnostic Probe for Diabetes Type I Predisposition" filed Oct. 29, 1987 describes a probe sequence which purportedly was specifically reactive with the DQB1 0302 sequences. However, subsequent HLA sequencing (see, Marsh and Bodmer, *Tissue Antigens*, 45:258–280 (1995), incorporated by reference herein) has revealed that the probe is not specific to DQB1 0302 allele. In fact, the disclosed probe reacts with nine of the twenty-five known DQB1 alleles, namely 0302, 03032, 0305, 0401, 0402, 05031, 05032, 06011, and 06012.

Accordingly, what is needed in the art are compositions and methods for specifically detecting all of the high risk alleles: DQB1 0201, 0202, 0302, 0303. Additionally, what is needed are compositions and methods for specifically detecting the risk reducing DQB1 allele 0602. More particularly, what is needed are compositions and methods to specifically and simultaneously detect the DQB1 alleles 0201, 0202, 0302, 0303, and 0602 under the uniform low-temperature assay conditions which are desirable for high volume clinical testing. Quite surprisingly, the present invention provides these and other advantages.

SUMMARY OF THE INVENTION

In one aspect, the present invention relates to a method of detecting the presence of HLA DQB1 alleles 0201/0202, 0302/0303, and 0602 in a human biological sample. The methods comprises the steps of contacting, under stringent conditions, an amplicon comprising a sequence from codon 23 through 40 of the human leukocyte antigen (HLA) DQB1 gene with at least three unique human leukocyte antigen (HLA) DQB1 allele-specific probes to form a hybridization complex and detecting the hybridization complexes as an indication of the presence of the HLA DQB1 alleles 0201/0202, 0302/0303, and 0602. In this aspect of the invention the amplicon is no more than 2000 base pairs in length and is amplified with at least two primers, wherein one of the two primers selectively hybridizes, under stringent conditions, to the same nucleic acid sequence of the HLA DQB1 allele as a primer having the sequence 5'-GGAGCGCGTGCGTCTTGTG-3' (SEQ ID NO:7). Further, the HLA DQB1 allele-specific probe is between 15 and 200 nucleotides in length, and each of the DQB1 allele-specific probes includes a nucleic acid segment of at least 15 contiguous nucleotides which selectively hybridizes under stringent conditions to the same nucleic acid sequence of the HLA DQB1 allele as an oligonucleotide selected from the group consisting of SEQ ID NOS: 2, 4, 6, and complementary sequences thereof. Each of the allele-specific probes selectively hybridizes under the same stringent hybridization conditions.

In some embodiments the amplicon is no longer than 1000 base pairs in length, in other embodiments the amplicon is no longer than 700 base pairs in length. In further embodiments, the nucleic acid segments selectively hybridize under stringent conditions to at least 18 contiguous bases of an oligonucleotide selected from the group consisting of: SEQ ID NO:2, SEQ ID NO:4, SEQ ID NO:6, and complementary sequences thereof. In preferred embodiments, the nucleic acid segment is complementary to an oligonucleotide selected from the group consisting of SEQ ID NO:2, SEQ ID NO:4, SEQ ID NO:6, and complementary sequences thereof. In a particularly preferred embodiment, the amplicon further comprises a sequence having any number of contiguous bases in the sequence from codon 22 to 41. Preferably, the amplicon is generated using a primer which selectively hybridizes, under stringent conditions, to the same nucleic acid sequence of the HLA DQB1 allele as a primer having the sequence 5'-TCTGGCTGTTCCAGTACTCGGC-3' (SEQ ID NO:8) in conjunction with a primer which selectively hybridizes, under stringent conditions, to the same nucleic acid sequence of the HLA DQB1 allele as a primer having the sequence shown in SEQ ID NO:7.

In another aspect, the present invention relates to a method of detecting the presence of HLA DQB1 alleles 0201/0202, 0302/0303, and 0602 in a human biological sample. The methods comprises the steps of contacting an amplicon comprising a sequence from codon 23 through 49 of the human leukocyte antigen (HLA) DQB1 gene with at least three unique human leukocyte antigen (HLA) DQB1 allele-specific probes to form a hybridization complex and detecting the hybridization complexes as an indication of the presence of the HLA DQB1 alleles 0201/0202, 0302/0303, and 0602. In this aspect of the invention, the amplicon is no more than 2000 base pairs in length and is amplified with at least two primers, wherein one of the two primers selectively hybridizes, under stringent conditions, to the same nucleic acid sequence of the HLA DQB1 allele as a primer having the sequence 5'-GGAGCGCGTGCGTCTTGTG-3' (SEQ ID NO:7). Further, the HLA DQB1 allele-specific probes is between 15 and 200 nucleotides in length, and each of the DQB1 allele-specific probes includes a nucleic acid segment of at least 15 contiguous nucleotides which selectively hybridizes under stringent conditions to the same nucleic acid sequence of the HLA DQB1 allele as an oligonucleotide selected from the group consisting of SEQ ID NOS: 1, 2, 3, 4, 5, 6, and complementary sequences thereof, with the proviso that each of the allele-specific probes selectively hybridizes under the same stringent hybridization conditions.

In some embodiments the amplicon is no longer than 1000 base pairs in length, in other embodiments the amplicon is no longer than 700 base pairs in length. In other embodiments, the nucleic acid segments selectively hybridize under stringent conditions to at least 18 contiguous bases of an oligonucleotide selected from the group consisting of: SEQ ID NO:2, SEQ ID NO:4, SEQ ID NO:6, and complementary sequences thereof. In preferred embodiments, the nucleic acid segment is complementary to an oligonucleotide selected from the group consisting of: SEQ ID NO:1, SEQ ID NO:2, SEQ ID NO:3, SEQ ID NO:4, SEQ ID NO:5, SEQ ID NO:6, and complementary sequences thereof. In a particularly preferred embodiment, the amplicon further comprises a sequence having any number of contiguous bases in the sequence from codon 22 to 50. Preferably, the amplicon is generated using a primer which selectively hybridizes, under stringent conditions, to the same nucleic acid sequence of the HLA DQB1 allele as a primer having the sequence 5'-TCTGGCTGTTCCAGTACTCGGC-3' (SEQ ID NO:8) in conjunction with a primer which selectively hybridizes, under stringent conditions, to the same nucleic acid sequence of the HLA DQB1 allele as a primer having the sequence shown in SEQ ID NO:7. In particularly preferred embodiments, the three unique DQB1 allele-specific probes have sequences shown in SEQ ID NO:1, 3, and 5, or SEQ ID NO:2, 4, and 6.

In another aspect, the present invention relates to a kit for detecting the presence of HLA DQB1 alleles 0201/0202, 0302/0303, and 0602 in a human biological sample. The kit comprises at least three probes of to 100 nucleotides in length. The probes comprise a nucleic acid segment which is complementary to the same nucleic acid sequence of the HLA DQB1 allele as an oligonucleotide selected from the group consisting of: SEQ ID NO:1, SEQ ID NO:2, SEQ ID NO:3, SEQ ID NO:4, SEQ ID NO:5, SEQ ID NO:6, and complementary sequences thereof.

The present invention has utility in determining the presence of HLA alleles which are associated with susceptibility to, or protection from, insulin dependent diabetes mellitus (IDDM or Type I diabetes).

DETAILED DESCRIPTION OF THE INVENTION

The present invention provides compositions and methods for specifically detecting the presence of the DQB1 0201/0202, 0302/0303, and 0602 alleles in a human biological sample. The method has utility in alerting the clinician to a patient's increased or decreased risk of developing IDDM. Using this information the clinician can, for example, increase monitoring of the patient's health and suggest changes in diet.

PCR primers of the present invention allow selective amplification of selected DQB1 alleles. Capture sequences of the present invention allow a subset of the amplified sequences to be detected. Surprisingly, although simultaneous detection of the aforementioned DQB1 requires discrimination between oligos with single base pair mismatches, the methods of the present invention allow detection of the alleles of interest with an unexpected degree of sensitivity and specificity.

The capture oligo sequences of the present invention will each resolve one and no more than one from the set of amplified alleles 0201/0202, 0302/0303 and 0602. However, they will not resolve other alleles such as 0401, 0402, 0503, 0601, and 0603. These alleles are excluded from amplification by mismatches within the forward PCR primer, SEQ ID NO: 7. These mismatches included a single 3' base pair mismatch which prevented amplification of the 0603, 0604, 0605, 0606, and 0609 alleles, and a two or three base pair mismatch five bases from the 3' end which prevented amplification of the 0301, 0304, 0401, 0402, 0501, 0503, and 0601 alleles.

It was surprising that a single set of PCR conditions could be found which would selectively exclude all of these alleles from amplification while not preventing the desired 0201, 0202, 0302, 0303, and 0602 alleles from amplification. This is especially true since some of these mismatches are in a less than optimal non-3'-terminal location. It was also surprising that the yield of the desired amplification products was sufficient due to the high stringency of the PCR conditions and the variable purity of the DNA isolated from clinical samples. Other unknowns such as the DNA secondary and tertiary structure (hairpins) and the uniqueness of the primers among all of the possible sequences within the human genome also did not prevent the desired selected allele amplifications.

Further, the probes and methods of the present invention prove surprisingly effective in specifically detecting multiple DQB1 alleles under uniform low-temperature assay conditions. These conditions are highly desirable in clinical laboratories where rapid diagnostic assays are required. Accordingly, the present invention permits a more efficient determination of the presence or absence of the tested alleles under conditions compatible with the high volume requirements of clinical laboratories.

Definitions

Units, prefixes, and symbols may be denoted in their SI accepted form. Unless otherwise indicated, nucleic acids are written left to right in 5' to 3' orientation. Numeric ranges are inclusive of the numbers defining the range. The terms defined immediately below are more fully defined by reference to the specification as a whole.

The term "nucleic acid" includes reference to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

The terms "isolated" or "biologically pure" include reference to material which is substantially or essentially free from components which normally accompany or interact with it as found in its naturally occurring environment. The isolated material optionally comprises material not found with the material in its natural environment.

The term "unique" includes reference to a nucleic acid segment which selectively hybridizes to one set, and only one set, from the three HLA DQB1 sets: 1) 0201/0202, 2) 0301/0302, and 3) 0602, where the "/" indicates that the nucleic acid segment selectively hybridizes, under stringent conditions, to either of the alleles in the set.

The term "HLA DQB1" includes reference to the B1 region of the β chain of a class II HLA protein coded for by the human leukocyte antigen (HLA) DQ gene.

The term "HLA DQB" includes reference to the β chain of a class II HLA protein coded for by the human leukocyte antigen (HLA) DQ gene.

The term "allele" includes reference to a variant of a gene or a region within a gene.

The term "HLA DQB1 allele-specific probes" includes reference to probes which selectively hybridize, under stringent hybridization conditions, to the HLA DQB1 allelic region to a detectably greater degree than to other nucleic acids in the human biological sample. Generally, selective hybridization provides a signal that is at least twice above background.

The terms "segment of nucleic acid" or "nucleic acid segment" includes reference to a nucleic acid sequence of between 10 to 75 nucleotides or nucleotide analogs in length or concatamers of such sequence.

The term "amplified" includes reference to the construction of multiple copies of a nucleic acid sequence or multiple copies complementary to the nucleic acid sequence using at least one nucleic acid sequence as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Ed. D. H. Persing et al., American Society for Microbiology, Washington, D.C.

The term "contiguous nucleotides" from a referenced nucleic acid includes reference to a sequence of nucleotides having the same order and directly adjacent to the same nucleotides (i.e., without additions or deletions) as in the referenced nucleic acid.

The term "oligonucleotide" probe includes reference to double stranded and/or single stranded DNA or RNA. The term also includes reference to synthetically or recombinantly derived sequences essentially free of non-nucleic acid contamination.

The term "complementary" in reference to two single-stranded nucleic acid sequences includes reference to contiguous nucleotides within the sequences are able to base pair and form a hybridization complex under stringent hybridization conditions intolerant of single base-pair mismatches within the base-paired region. The contiguous regions are "complements" of each other. Complementary sequences are from 15 to 200 nucleotides in length, and preferably from 18 to 50 nucleotides in length. The rules of purine:pyrimidine base pairing (e.g., G:C, A:T, A:U) for nucleosides and nucleoside analogs are known in the art. See, e.g., *Recombinant DNA*, Watson et al. (eds.), Scientific American Books, New York, N.Y. (1992).

The term "selectively hybridizes under the same stringent hybridization conditions" in reference to "unique" nucleic acids is meant that under a particular stringent hybridization condition each of the unique nucleic acids is able to selectively hybridize to its complement to a detectably greater degree than to non-complementary nucleic acids. Generally, the unique nucleic acids are able to selectively hybridize to their complements at least 2-fold greater than to non-complementary nucleic acids. Preferably, at least 5-fold greater, more preferably at least 10-fold greater.

The terms, "contact" or "contacting" includes reference to placing in direct physical association.

The term "amplicon" includes reference to an "amplified" nucleic acid.

The term "codon" includes reference to a nucleotide triplet encoding an amino acid according to the universal genetic code.

The term "hybridization complex" includes reference to a duplex nucleic acid sequence formed by selective hybridization of two single-stranded nucleic acids with each other.

The term "nucleotides in length" in reference to a particular nucleic acid sequence includes reference to a sequence which has the indicated number of nucleotides covalently linked in 5' to 3' fashion.

The term "base pairs in length" includes reference to the length of a duplex nucleic acid structure measured in terms of the number of contiguous nucleotide bases which are paired.

The term "primer" includes reference to a nucleic acid sequence which comprises a complementary nucleic acid sequence to a target nucleic acid and is able to initiate nucleic acid strand elongation by a DNA or RNA polymerase using the target as a template for base pairing. Primers are at least 15 nucleotides in length, more typically at least 17, 18, or 19 nucleotides in length, and preferably at least 20, 21, 22, 23, 24 or 25 nucleotides in length.

The term "amplicon is generated" in reference to a specified primer includes reference to the use of the specified primer to initiate DNA or RNA polymerization from a template strand to form an amplicon.

The terms "stringent conditions" or "stringent hybridization conditions" include reference to conditions under which a probe will hybridize to its target subsequence, but to no other sequences. Stringent conditions are sequence-dependent and will be different in different circumstances. Longer sequences hybridize specifically at higher temperatures. Stringent conditions are within 5° C. (±5° C.) of the thermal melting point (Tm) for the specific sequence at a defined ionic strength and pH. Generally, stringent conditions are selected to be about 5° C. lower than the thermal melting point (Tm). The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is about 1.0 M Na ion (or other salts) at pH 7.0 to 8.3 and the temperature is 5° C. less than Tm, where Tm in centigrade is 2×A+T content +4×G+C content of the contiguous length of sequence of probe/target duplex for short probes (e.g., 10 to 50 nucleotides). Stringent conditions of lower temperature may also be achieved with the addition of destabilizing agents such as formamide or guanidine thiocyanate.

"Stringent hybridization conditions" or "stringent conditions" in the context of nucleic acid hybridization assay formats are sequence dependent, and are different under different environmental parameters. An extensive guide to the hybridization of nucleic acids is found in Tijssen (1993) *Laboratory Techniques in Biochemistry and Molecular*

*Biology—Hybridization with Nucleic Acid Probes* Part I, Chapter 2 "Overview of principles of hybridization and the strategy of nucleic acid probe assays", Elsevier, New York. Stringent conditions are sequence-dependent and will be different in different circumstances. Longer sequences hybridize specifically at higher temperatures.

As used herein, "human biological sample" is a sample of biological tissue or fluid from a human that contains an HLA DQB1 nucleic acid. Such samples include, but are not limited to, sputum, amniotic fluid, blood, blood cells, or tissue. Biological samples may also include sections of tissues such as frozen sections taken for histological purposes or cultured human cells.

The term "detecting" includes reference to quantitatively or qualitatively determine the extent or degree of.

The terms "selectively hybridizing" or "selective hybridization" include reference to hybridization, under stringent hybridization conditions, of a nucleic acid sequence to a specified nucleic acid target sequence to a detectably greater degree than its hybridization to non-target nucleic acid sequences. Selectively hybridizing sequences have 100% sequence identity (i.e., complementary) with each other. "Percentage of sequence identity" is determined by comparing two optimally aligned sequences over the length of the compared sequences, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Nucleic Acid Probes

The present invention provides nucleic acid compositions for detecting, in a human biological sample, the presence or absence of the human leukocyte antigen (HLA) alleles: 0201/0202, 0302/0303, and 0602. Sequences of these alleles are known in the art. See, e.g., *Tissue Antigens* 45:258–280 (1995). The nucleic acid compositions comprise at least two, preferably three, isolated HLA DQB1 probes each of which are specific in selectively hybridizing, under stringent conditions, to one set of the three sets of HLA DQB1 alleles: 1) 0201/0202, 2) 0302/0303, and 3) 0602. The "/" indicates that either of the alleles in the specified set will selectively hybridize under stringent conditions to the probe since the alleles have 100% sequence identity in the region of hybridization with the nucleic acid segment. Those of skill will recognize that one or two different DQB1 alleles will be encoded for in a diploid genome (i.e., one DQB1 allele per haploid chromosome set). The HLA DQB1 allele-specific probes of the present invention may be a composition of RNA or DNA or chimera thereof. In addition, analogs of nucleosides may be substituted for naturally occurring nucleosides. The advantage of analogs would include greater stability, resistance to nuclease activity and ease of signal attachment.

In addition to being specific to the DQB1 region, each of the probes is unique from the other HLA DQB1 allele-specific probes in the composition in that each probe includes a nucleic acid segment which selectively hybridizes, under stringent conditions, to no more than one set of alleles from the 3 sets: 1) 0201/0202, 2) 0302/0303, and 3) 0602. The HLA allele-specific probes of the present invention selectively hybridize under the same stringency conditions (i.e., have similar melting temperatures). To achieve this, the probes preferably employed hybridize to the same nucleic acid sequences as oligonucleotides of SEQ ID NOS: 1, 3, and 5, or SEQ ID NOS: 2, 4, and 6. Oligonucleotides of SEQ ID NOS: 1, 3, and 5 have the same Tm with their complementary sequences as do oligonucleotides of SEQ ID NOS: 2, 4, and 6.

Those of skill in the art will recognize that while an HLA allele-specific probe may include multiple nucleic acid segments, each of the segments will be unique to the same allele. Thus, probes of the present invention will not cross-hybridize to more than one set of alleles from the three sets: 1) the 0201/0202 alleles, 2) the 0302/0303 alleles, and 3) the 0602 alleles. The probe is at least N nucleotides in length where N is any one of the integers selected from the group consisting of from 15 to 200. Generally, the probe is at least 18 nucleotides in length, preferably at least 19, 20, 21, 22 or 23 nucleotides in length.

The probe includes a nucleic acid segment of at least N' nucleotides in length, where N' is any one of the integers selected from the group consisting of from 15 to 75 nucleotides. The nucleic acid segment selectively hybridizes, under stringent conditions, to the same nucleic acid sequence of the HLA DQB1 allele as an oligonucleotide selected from the group consisting of: for the 0201/0202 alleles 5'-CGTGGGGGAGTTCCGGGCGGTG-3' (SEQ ID NO:1) or 5'-AAGAGATCGTGCGCTTCGACA-3' (SEQ ID NO:2); for the 0302/0303 alleles 5'-CGTGGGGGTGTATCGGGCGGTG-3' (SEQ ID NO:3) or 5'-AGGAGTACGCACGCTTCGACA-3' (SEQ ID NO:4); for the 0602 allele 5'-CGTGGGGGTGTACCGCGCGGTG-3' (SEQ ID NO:5) or 5'-GGAGTACGCGCGCTTCGAC-3' (SEQ ID NO:6), and complementary sequences of SEQ ID NOS:1 through 6. Typically, the nucleic acid segment is at least 18, 19, 20, 21, or 22 nucleotides in length. Preferably, the nucleic acid segments comprise a nucleic acid sequence shown in SEQ ID NO:1, 2, 3, 4, 5, 6, or the complementary sequences of SEQ ID NO:1, 2, 3, 4, 5, or 6.

As will be understood by those of skill in the art, the length of the HLA DQB1 allele-specific probe should generally be as short as is necessary for the desired purpose. Moreover, probe sequences which do not constitute the nucleic acid segment should not selectively hybridize, under stringent conditions, to the nucleic acid segments of the HLA DQB1 allele-specific probes (and possibly lead to a false negative by preventing hybridization to the DQB1 allele), neither should non-nucleic acid segment probe sequences substantially cross-hybridize, under the stringent conditions of an assay, with nucleic acids whose presence in the human biological sample would lead to a false positive. For example, non-nucleic acid segments of the probe should not substantially hybridize, under stringent conditions of the assay, to those HLA alleles (or other human nucleic acid sequences) whose presence is the sample are not being assayed for. "Not substantially" means to a detectably lesser extent than selective hybridization, under stringent conditions, between the nucleic acid segment of the probe and its DQB1 target allele. Typically, this refers to hybridization at least half that of a positive control.

Assays for determining the compatibility of a particular sequence in a nucleic acid assay are known as are the use of positive controls, negative controls, and/or procedural controls to ensure selective detection of the HLA DQB1 alleles of interest. Moreover, a large number of human nucleic acid sequences are accessible in databases (e.g., GenBank or EMBL). These sequences can be tested using commercially available software for potential hybridization, under stringent conditions, with any nucleic acid sequence region outside of the nucleic acid segment of the probe. Additionally, the human biological sample can be treated to remove potentially cross-hybridizing sequences (e.g., subtractive hybridization), or the sample may be enriched for HLA DQB1 allelic regions of interest (e.g., PCR amplification of 0201/0202, 0302/0303, or 0602) to dilute potentially interfering sequences.

The HLA DQB1 allele-specific probes of the nucleic acid composition are designed to selectively hybridize under the same stringent conditions. Thus, the melting temperatures of the probes are chosen to be substantially similar. Generally, the range of melting temperature of the probes is no greater than 5° C., preferably no greater than 4° C., 3° C., or 2° C., more preferably no greater than 1° C., most preferably less than 1° C. Computer algorithms for determining the melting temperatures of probes under defined ion concentrations is known in the art (See, e.g., the commercially available computer program OLIGO (Version 3.3), Research Genetics, Huntsville, Ala.).

While many sequences can be used to construct primers, selecting optimal amplification primers is typically done using a computer to assist in the selection of primer sequences having the desired hybridization characteristics. This is done by computer screening of primers, with desired hybridization properties (e.g., those with a selected length and G:C ratio) based upon the known sequence. The selection of the hybridization properties of the primer is dependent on the desired hybridization and discrimination properties of the primer. In general, the longer the primer, the higher the melting temperature. However, longer primers are not as specific because a single mismatch has less of a destabilizing effect on hybridization than a single mismatch on a short nucleic acid duplex; thus, long primers can create unwanted PCR products. It is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology— hybridization with nucleic acid probes*, e.g., part I chapter 2 "Overview of principles of hybridization and the strategy of nucleic acid probe assays", Elsevier, New York. provide a basic guide to nucleic acid hybridization. Innis et al. (*PCR Protocols. A Guide to Methods and Application* (Academic Press, Inc., San Diego, Calif. 1990)) provides an overview of primer selection.

The isolated nucleic acid compositions of this invention, whether RNA, DNA, or a hybrid of the two, are isolated from biological sources or synthesized in vitro. Cloning methodologies to accomplish these ends, and sequencing methods to verify the sequence of nucleic acids are well known in the art. For example, to obtain large quantities of probes, one can insert a nucleic acid encoding a probe of the present invention into a replication vector, such as pBR322, M13, or into a vector containing the SP6 promotor (e.g., generation of single-stranded RNA using SP6 RNA polymerase), and transformation of a bacterial host. The DNA probes can be purified from the host cell by lysis and nucleic acid extraction, treatment with selected restriction enzymes, and further isolation by gel electrophoresis. Examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Deoxynucleotides may be synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Nucleic Acid Assays

The present invention provides a method of detecting in a human biological sample the presence of the HLA DQB1 alleles: 0201/0202, 0302/0303, or 0602. As will be understood by those of skill in the art, selective hybridization of a nucleic acid probe to the target single-stranded complementary sequence in a sample will yield a hybridization complex (comprising a duplex structure). Detection of the hybridization complex is an indication of the presence of the target sequence in the sample.

In one aspect of the method of the present invention, an amplicon encoding the sequence from codon 23 through codon 41 is contacted, under stringent conditions, with at least two unique HLA DQB1 allele-specific probes. The codon numbering is as provided in *Tissue Antigens* 45:258 (1995), incorporated herein by reference. Each of the probes selectively hybridizes, under stringent conditions, to one set, and no more than one set, of HLA DQB1 alleles from the three sets: 1) 0201/0202, 2) 0302/0303, and 3) 0602. Thus in addition to being specific, the probes are unique in that they selectively hybridize, under stringent conditions, to a different set of HLA DQB1 alleles (i.e., the target allele(s)) to a detectably greater degree than non-DQB1 alleles. Preferably, at least three unique HLA DQB1 allele-specific probes are employed in the method. These three unique probes selectively hybridize, under stringent conditions, to the three allele sets: 1) 0201/0202, 2) 0302/0303, and 3) 0602. Selective hybridization by the HLA DQB1 probes of the present invention to its target allele(s) leads to formation of a hybridization complex.

The features of the HLA DQB1 allele-specific probes of the present invention are discussed more fully above. As indicated therein, each of the HLA DQB1 allele-specific probes includes a nucleic acid segment of at least 15 nucleotides in length which selectively hybridizes, under stringent conditions, to the same nucleic acid sequence of an HLA DQB1 allele as an oligonucleotide selected from the group consisting of: for the 0201/0202 alleles 5'-AAGAGATCGTGCGCTTCGACA-3' (SEQ ID NO:2); for the 0302/0303 alleles 5'-AGGAGTACGCACGCTTCGACA-3' (SEQ ID NO:4); for the 0602 allele 5'-GGAGTACGCGCGCTTCGAC-3' (SEQ ID NO:6), and complementary sequences of SEQ ID NOS:2, 4, and 6. In preferred embodiments, the probes have the sequences shown in SEQ ID NOS: 2, 4, and 6.

The amplicon comprising the sequence from codon 23 through 41 is N" nucleotides in length, where N" is an integer selected from any one of the integers from 18 to 2000. Typically, the amplicon is no more than 1500 nucleotides in length, preferably no more than 1000 nucleotides in length, more preferably no more than 700, and most preferably no more than 200 nucleotides in length. In preferred embodiments, the amplicon comprises the sequence from codons 23 to 40 further comprises any number of contiguous nucleotides extending upstream to codon 22. In particularly preferred embodiments, the amplicon is amplified using a primer which selectively hybridizes, under stringent conditions, to the same nucleic acid sequence of the HLA DQB1 allele as a primer having the sequence of SEQ ID NO:7.

In another aspect, the present invention provides a method of detecting the presence of HLA DQB1 alleles 0201/0202, 0302/0303, and 0602 in a human biological sample. While the various embodiments of this aspect, or any other aspect, of the invention may generally be had by reference to the specification as a whole, in this aspect of the invention the amplicon comprises the sequence from codon 23 through 50 of the HLA DQB1 gene. The amplicon is contacted, under stringent conditions, with at least two unique HLA DQB1 alleie-specific probes. Each of the probes selectively hybridizes, under stringent conditions, to one and no more than one set of HLA DQB1 alleles from the three sets: 1) 0201/0202, 2) 0302/0303, and 3) 0602. Preferably, at least three unique HLA DQB1 allele-specific probes are employed in the method which selectively hybridizes, under stringent conditions, to each of the three sets of DQB1 alleles.

The amplicon is contacted with a DQB1 allele-specific probe which includes a nucleic acid segment of at least 15 nucleotides in length which selectively hybridizes under stringent conditions to the same nucleic acid sequence of the HLA DQB1 allele as an oligonucleotide selected from the group consisting of: for the 0201/0202 alleles 5'-CGTGGGGGAGTTCCGGGCGGTG-3' (SEQ ID NO: 1), for the 0302/0303 alleles 5'-CGTGGGGGTGTATCGGGCGGTG-3' (SEQ ID NO:3), for the 0602 allele 5'-CGTGGGGGTGTACCGCGCGGTG-3' (SEQ ID NO:5), and complementary sequences of SEQ ID NOS: 1, 3, and 5. In preferred embodiments, the nucleic acid segment selectively hybridizes under stringent conditions to the same nucleic acid sequence of the HLA DQB1 allele as an oligonucleotide selected from the group consisting of: for the 0201 and 0202 alleles 5'-CGTGGGGGAGTTCCGGGCGGTG-3' (SEQ ID NO:1), 5'-AAGAGATCGTGCGCTTCGACA-3' (SEQ ID NO:2), for the 0302/0303 alleles 5'-CGTGGGGGTGTATCGGGCGGTG-3' (SEQ ID NO:3), 5'-AGGAGTACGCACGCTTCGACA-3' (SEQ ID NO:4), for the 0602 allele 5'-CGTGGGGGTGTACCGCGCGGTG-3' (SEQ ID NO:5), 5'-GGAGTACGCGCGCTTCGAC-3' (SEQ ID NO:6), and complementary sequences of SEQ ID NOS: 1, 2, 3, 4, 5, and 6. Combinations of the various probes or their complements can be employed as desired. Moreover, either single or multiple probes can be used to selectively hybridize to the target alleles. For example, probes which selectively hybridizes to the same nucleic acid as an oligonucleotide of SEQ ID NO:1 can be used independent of or in combination with a probe which selectively hybridizes to the same nucleic acid as an oligonucleotide of SEQ ID NO:2; these probes detect the target allele 0201/00202. Probes which selectively hybridize to the same nucleic acid as an oligonucleotide of a nucleic acid of SEQ ID NO:3 can be used independent of or in combination with a probe which selectively hybridizes to the same nucleic acid as an oligonucleotide of SEQ ID NO:4; these probes detect the target allele 0302/0303. Probes which selectively hybridizes to the same nucleic acid as an oligonucleotide of SEQ ID NO:5 can be used independent of or in combination with a probe which selectively hybridizes to the same nucleic acid as an oligonucleotide of SEQ ID NO:6; these probes detect the target allele 0602.

In some embodiments, the nucleic acid segments selectively hybridize, under stringent conditions, to at least 18 contiguous bases of an oligonucleotide selected from the group consisting of: SEQ ID NOS: 1, 2, 3, 4, 5, 6, and complementary sequences thereof. In preferred embodiments, the nucleic acid segment is complementary to an oligonucleotide selected from the group consisting of: SEQ ID NO: 1, 2, 3, 4, 5, 6, and complementary sequences of SEQ ID NOS: 1, 2, 3, 4, 5, and 6. Generally, the amplicon comprising the sequence from codon 23 to codon 50 will further comprise any number of contiguous nucleotides extending upstream to codon 22. In particularly preferred embodiments, the nucleic acid assays of the present invention are performed using probes having the sequences shown in SEQ ID NOS: 1, 2, 3, 4, 5, and 6, wherein probes of SEQ ID NO:2, 4, and 6, or probes of SEQ ID NO: 1, 3, and 5 are used in combination. Probes having the sequences shown in SEQ ID NOS: 1, 3, and 5, or 2, 4, and 6 have substantially similar melting temperatures.

The means of generating the amplicon are not a critical aspect of the invention. In preferred embodiments, the amplicon is generated using the PCR. For a review of PCR methods and protocols, see, e.g., Innis, et al. eds. *PCR Protocols. A Guide to Methods and Application* (Academic Press, Inc., San Diego, Calif. 1990). PCR reagents and protocols are also available from commercial vendors, such as Roche Molecular Systems. Briefly, the first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965,188). Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis.

In preferred embodiments of the method of the present invention, the amplicon is generated using as one of the primers, a primer which selectively hybridizes, under stringent conditions, to the same nucleic acid sequence of the DQB1 allele as a primer having the sequence 5'-GGAGCGCGTGCGTCTTGTG-3' (SEQ ID NO:7), which amplifies starting from codon 22. Primers which, in conjunction with a primer of SEQ ID NO:7, amplify a region up to at least codon 40 may be designed using published HLA sequences (Marsh and Bodmer, *Tissue Antigens,* 45:258–280 (1995)). Those of skill understand that primers should be of sufficient length to selectively hybridize to the desired HLA region under amplification conditions. In particularly preferred embodiments, the amplicon is generated using SEQ ID NO:7 in combination with a primer which selectively hybridizes, under stringent conditions, to the same nucleic acid sequence of the DQB1 allele as a primer having the sequence 5'-TCTGGCTGTTCCAGTACTCGGC-3' as shown in SEQ ID NO:8. Preferably, primers of the present invention have the sequence shown in SEQ ID NO:7 and/or SEQ ID NO:8. Optionally, the primers may include 5' sequences no more than 50 nucleotides in length, and preferably no more than 25 nucleotides in length. The additional sequence may be complementary or non-complementary (e.g., a primer "tail") to the target allele.

Hybridization Format and Conditions

A variety of nucleic acid hybridization formats are known to those skilled in the art and may be used in the methods of the present invention. For example, common formats include sandwich assays and competition or displacement assays. Hybridization techniques are generally described in Berger and Kimmel, (1987), supra.; *"Nucleic Acid Hybridization, A Practical Approach"* (Hames, B. D. and Higgins, S. J. (eds.), IRL Press, 1985; Gall and Pardue, (*Proc. Natl. Acad. Sci.,* U.S.A. 63:378–383 (1969)); and John, Burnsteil and Jones (*Nature,* 223:582–587 (1969)). In a preferred embodiment, the hybridization assay method used is described in a commonly assigned patent application filed on an even date herewith and bearing Ser. No. 60/037,426, the teachings of which are incorporated herein by reference.

Sandwich assays are commercially useful hybridization assays for detecting or isolating nucleic acid sequences. Such assays utilize a "capture" nucleic acid covalently immobilized to a solid support and a labelled "signal" nucleic acid in solution. The biological sample will provide the target nucleic acid. The "capture" nucleic acid probe and the "signal" nucleic acid probe hybridize with the target nucleic acid to form a "sandwich" hybridization complex. To be effective, the signal nucleic acid cannot hybridize with the capture nucleic acid.

In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4(3):230–250 (1986); Haase et al., *Methods in Virology,* Vol. VII, pp. 189–226 (1984); Wilkinson, "The theory and practice of in situ hybridization" In: *In situ Hybridization,* Ed. D. G. Wilkinson. IRL Press, Oxford University Press, Oxford; and *Nucleic Acid Hybridization: A Practical Approach,* Ed. Hames, B. D. and Higgins, S. J., IRL Press (1987).

Methods of isolating total DNA or mRNA from human cells for use in a nucleic acid assay are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, New York. (1993).

Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The hybridization format or buffers are not critical aspects of the present invention and those of skill will recognize that further advances, improvements, or modifications in nucleic acid hybridization, amplification, and detection are within the scope of the invention.

Detection

The means by which hybridization complexes are detected is not a critical aspect of the present invention and can be accomplished by any number of methods currently known or later developed. Nucleic acid probes capable of selectively hybridizing to the HLA DQB1 alleles of interest can be labeled by any one of several methods typically used to detect the presence of hybridized nucleic acids. Detectable labels suitable for use in the present invention include any composition detectable by spectroscopic, radioisotopic, photochemical, biochemical, immunochemical, electrical, optical or chemical means. One common method of detection is the use of autoradiography using probes labeled with $^3H$, $^{125}I$, $^{35}S$, $^{14}C$, or $^{32}P$, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I, by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorosphore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelli-ferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody. In a preferred embodiment, the label is simultaneously incorporated during the amplification step in the preparation of the nucleic acids. Thus, for example, polymerase chain reaction (PCR) with labeled primers or labeled nucleotides will provide a labeled amplification product. In another preferred embodiment, transcription amplification using a labeled nucleotide (e.g., fluorescein-labeled UTP and/or CTP) incorporates a label into the transcribed nucleic acids.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Kits

The HLA DQB1 allele-specific probes of this invention can be included in a kit which can be used to rapidly determine the presence of the HLA DQB1 alleles 0201, 0202, 0302, 0303, and 0602 in a human biological sample. The kit typically includes all components necessary to assay for the presence of at least three sets of alleles from the sets: 1) 0201/0202, 2) 0302/0303, and 3) 0602 in a human biological sample. The kit generally includes a stable preparation of at least 2, and usually 3, 4, 5, or 6 HLA DQB1 allele-specific probes of the present invention. Typically, the kit also includes primers of SEQ ID NO:7 and/or SEQ ID NO:8. In preferred embodiments, the kit includes probes having the sequences shown in SEQ ID NOS: 1, 3, and 5, and/or SEQ ID NOS: 2, 4, and 6. Further, the kit may also include hybridization solution in either dry or liquid form for performing the method of the invention as well as a solution for washing and removing undesirable and non-hybridized nucleic acids, a substrate for detecting the hybridization complex, and/or instructional materials. In a preferred embodiment, the kit also includes the hybridization assay apparatus described in a commonly assigned patent application No. 60/037,426, filed Feb. 21, 1997.

Although the present invention has been described in some detail by way of illustration and example for purposes of clarity of understanding, it will be obvious that certain changes and modifications may be practiced within the scope of the appended claims.

EXAMPLE 1

Example 1 describes a bead based dipstick assay of DNA extracted from the white cells of 163 patents who were previously typed as to their HLA DQB1 alleles by RFLP or dot blot analysis.

As a forward primer for PCR amplification, the sequence GGAGCGCGTGCGTCTTGTG (SEQ ID NO:7) spanning codons 22–27 in the HLA DQB1 alleles was used. For the reverse primer the sequence 5'-TCTGGCTGTTCCAGTACTCGGC-3' (SEQ ID NO:8) spanning codons 58–64 was used. Because of the sequence differences in the region of the forward primer only the DQB1 0201, 0202, 0302, 0303, and 0602 alleles will amplify under the PCR conditions used. To selectively capture the DQB1 0201 and 0202 alleles, which have the similar predictive value, a sequence 5'-CGTGGGGGAGTTCCGGGCGGTG-3' (SEQ ID NO:1) spanning codons 44–50 or 5'-AAGAGATCGTGCGCTTCGACA-3' (SEQ ID NO:2) spanning codons 35–41 was used. To selectively capture the 0302 and 0303 alleles which also have similar predictive value, the sequence 5'-CGTGGGGGTGTATCGGGCGGTG-3' (SEQ ID NO:3) or 5'-AGGAGTACGCACGCTTCGACA-3' (SEQ ID NO:4) in the same codon regions as above was used. To selectively capture the 0602 allele, the sequence 5'-CGTGGGGGTGTACCGCGCGGTG-3' (SEQ ID NO:5) or 5'-GGAGTACGCGCGCTTCGAC-3' (SEQ ID NO:6) in the same codon regions was used. The melting temperature of oligos of SEQ ID NOS:1, 3, and 5, and SEQ ID NOS:2, 4, and 6, with their compliments are designed to be substantially similar allowing them to hybridize under the same conditions of assay stringency. Using these primers and capture oligos in a solid phase hybridization assay, the expected specificity and sensitivity necessary for a clinically useful assay was demonstrated.

As controls, to ensure assay reliability, the forward primer 5'-AGGCCGAGTTCTATCTGAATCCTGACC-3' (SEQ ID NO:9) spanning codons 9–17 in the HLA DRA 0101 allele and the reverse primer 5'-CCTCTGGAGGTACATTGGTGATCGG-3' (SEQ ID NQ:10) spanning codons 81–88 were used. To selectively capture this amplification product, the sequence GCCGC-CAGACCGTCTCCTTCTTTGCC (SEQ ID NO: 11) spanning codons 36–44 or CCGCCAGACCGTCTCCTTCT (SEQ ID NO:12) spanning codons 38–44 was used. Unlike the DQB1 gene family, humans only have a single DRA gene sequence in this region. Therefore, this amplification product was used as a control for the quality of the sample DNA and the validity of the PCR reagents. Digested DNA during sample extraction or the presence of PCR inhibitors which would prevent the DQB1 amplification would also prevent the DRA amplification. Therefore, if the DRA amplification occurs, then the absence of a 0201, 0202, 0302, 0303, 0602 result can be interpreted as the presence of the other DQB1 alleles rather than a faulty PCR reaction. Also included in the test was a synthetic oligo which is complementary to a positive control capture sequence. If all of the detection reagents were performing properly, this added control oligo will be detected. Finally, a capture sequence which is a single base mismatch with the added positive control oligo was used. The conditions of the hybridization reactions were set to enable a discrimination of a single base mismatch. Therefore this capture sequence should be negative if the hybridization reagents and temperature were correct.

One µl of extracted patient DNA was added to a PCR tube containing 44 µl of Cocktail A [35.3 µl of distilled water, 4.5 µl of 100 mM Tris-HCl, 15 mM MgCl$_2$, pH 8.3, 0.2 µl of 25 mM deoxynucleoside triphosphate (dNTPs), and 1 µl of each of the 10 mM primers]. The tube was placed in a pre-heated thermocycler at 80° C. for 5–10 min and overlaid with a drop of mineral oil. Five microliters of Cocktail B [4.12 µl distilled water, 0.5 µl of 100 mM Tris-HCl, 15 mM MgCl$_2$, pH 8.3, and 0.38 µl Taq DNA polymerase (5 U/µl)] was added. The thermocycler program consisted of the following order of steps: 94° C. for 5 min followed by 38 cycles of 94° C. 1 min, 68° C. 0.5 min, 72° C. 0.75 min, stopping with 72° C. for 5 min, and holding at 4° C. The tubes were removed and stored at 4° C. until ready for analysis.

The samples were analyzed by placing 20 µl of the PCR product into well 1 (containing 60 mM NaOH to denature the double stranded amplicon) of an 8-well pre-filled cassette placed on an automated sample processor which controls the temperature in the first three wells at 64–65° C. A dipstick containing press fit nylon beads which have allele-specific and control oligos attached was placed in well 2. Ninety µl of a neutralizing reagent (1 M NaH$_2$PO$_4$, pH 4.0) was added to well 1 and the processor program was started. The processor picked up the dipstick from well 2 and moved it through the eight wells of reagents in a time controlled manner. Thirty-seven minutes later the process was complete and any blue color on the beads indicated whether an allele was present or not.

The well components, their volumes and the program steps and times are described in the Table I:

TABLE I

| WELL # | CONTENTS | VOLUME µl | PRGM. STEP | TIME min. |
|---|---|---|---|---|
| 1 | 60 mM NaOH | 815 | 1 | 10 |
| 2 | 0.1 M Na$_2$HPO$_4$, pH 7.24 | 900 | 2 | 2 |
| 3 | 0.1 M Na$_2$HPO$_4$, pH 7.24 | 900 | 3 | 1 |
| 4 | 0.1 M Na$_2$HPO$_4$, pH 7.24 | 900 | 4 | 1 |
| 5 | streptavidin-peroxidase conjugate | 900 | 5 | 5 |
| 6 | Wash buffer* | 900 | 6 | 3 |
| 7 | Wash buffer* | 900 | 7 | 2 |
| 8 | TMB-ELISA | 900 | 8 | 10 |

*Wash buffer is 10 mM Tris, 1 mM EDTA, 91 mM NaCl, 35 mM SDS, and 34 mM N-Lauryl Sarkosyl, pH 8.0.

The capture beads on the dipstick from the bottom to the top are shown in the Table II:

TABLE II

| BEAD # | SPECIFICITY | INTERPRETATION OF A BLUE BEAD |
|---|---|---|
| 1 | Negative control | INVALID TEST, NON-SPECIFIC-BINDING OR LOW STRINGENCY |
| 2 | DQB1 0302/0303 | GREATER RISK OF IDDM |
| 3 | DQB1 0202/0202 | GREATER RISK OF IDDM |
| 4 | DQB1 0602 | REDUCED RISK OF IDDM |
| 5 | DRA 0101 | VALID PCR AMPLIFICATION |
| 6 | Positive control | VALID REAGENT CASSETTE |

In this example, the capture oligos spanning codons 44–50 described above were covalently attached to a polyethylene imine modified nylon bead using a hexylamine spacer attached to the oligo (see Nucleic Acids Research 19:3345 (1991)). Following the stringent hybridization of the PCR product in well 1 at 64° C. and stringent washes in wells 2 and 3, the captured product on the bead was exposed in well 5 to a streptavidin-peroxidase conjugate which can bind to a 5'-terminal biotin which was attached to the PCR primers. Following washing of the dipstick to remove the excess conjugate, in wells 6 and 7, the presence of the specific PCR product was visualized by the peroxidase catalyzed precipitation of a blue dye onto the bead in well 8. The precipitation was localized such that only the beads which bound PCR product or control oligo would turn blue.

The results of the preclinical study from the 163 previously typed patient samples are shown in the Table III.

TABLE III

| SAMPLE TYPE | # FROM PREVIOUS TYPING | # FOUND USING THIS TEST | # OF ERRORS | % CORRECT | REPEAT TEST % CORRECT |
|---|---|---|---|---|---|
| 0201 | 57 | 57 | 0 | 100% | 100% |
| 0302 | 35 | 37 | 2 | 95% | 100% |
| 0303 | 9 | 9 | 0 | 100% | 100% |
| 0602 | 40 | 39 | 1 | 98% | 100% |
| OTHER | 22 | 21 | 1 | 95% | 100% |
| TOTALS | 163 | 163 | | | |

The results in this table indicate that this test agrees with the previous typing of these samples in all but two of the 163 samples, a 602 sample and an "other" sample were both typed as 0302. When fresh samples of these two discrepant samples were re-amplified and retested the results then all agreed with the previous typing. It was concluded that during the first testing these two samples were either mislabeled or contaminated.

EXAMPLE 2

Example 2 describes the analysis of samples containing the DQB1 alleles 0201, 0302, and 0602 in a microwell format using an universal solid phase and comparing the results with the bead based dipstick assay described in Example 1.

The PCR conditions were the same as in Example 1 except that the PCR primers had a 5'-fluorescein attached rather than the 5'-biotin. The capture probes spanned codons 35–41 as described above. These capture probes had a biotin followed by two 18 atom spacers attached to the 5' ends of the capture oligo. The solid phase was a polystyrene dipstick to which was adsorbed streptavidin. The cassette consisted of a microwell strip filled with the following reagents through which the dipstick was moved in the programmed steps and times as indicated in Table IV:

TABLE IV

| WELL # | VOLUME µl | WELL CONTENTS | PRGM. STEP | TIME MIN. |
|---|---|---|---|---|
| 1 | | EMPTY | 3 | 10 |
| 2 | 150 | 2.6 M GuSCN, 17 mM EDTA, 1.76 M FORMAMIDE, 83 mM TRIS, pH 7.5 | 2 | 2 |
| 3 | 150 | CAPTURE PROBES IN 0.1 M Na$_2$HPO$_4$ 0.5% TWEEN-20, pH 7.2 | 1 | 10 |
| 4 | 150 | ANTI-FLUORESCEIN-PEROXIDASE CONJUGATE | 5 | 5 |

TABLE IV-continued

| WELL # | VOLUME µl | WELL CONTENTS | PRGM. STEP | TIME MIN. |
|---|---|---|---|---|
| 5 | 200 | 0.1 M Na₂HPO₄, 0.5% TWEEN-20, pH 7.2 | 4,6 | 1,1 |
| 6 | 200 | 0.1 M NaCl, 0.05 M TRIS, 0.5% CTAB, pH 8.0 | 7 | 1 |
| 7 | 200 | 0.1 M NaCl, 0.05 M TRIS, 0.5% CTAB, pH 8.0 | 8 | 1 |
| 8 | 150 | TMB EIA | 9 | 8 |

The assay was started by placing the 8-well microwell strip on the processor platform which controls the temperature in all of the wells at 30 C. Ten µl of sample was added to 0.5 ml of the 2.6 M guanidine thiocyanate buffer and the tube was heated at 85 C. to denature the double stranded amplicon. The streptavidin coated dipstick was placed on the processor arm and the program was started. The dipstick was moved to well 3 where it bound the biotin labeled capture oligo. Next, the excess capture oligo and any loosely bound oligo was removed by a stringent wash in well 2. Twelve minutes from the start the heated sample was added to well 1. The sample (0.1 ml) was added to each of four strips. Each strip has a capture oligo in well 3 which was specific for either the DQB1 0201/0202 alleles, the 0302/0303 alleles, the 0602 allele, or the DRA allele. The program was again started. The solid phase hybridized amplification product from well 1 was washed in well 5 and moved to the anti-fluorescein-peroxidase conjugate where it bound to any fluorescein labeled PCR primer present on the dipstick. The excess conjugate was washed off of the dipstick in wells 5–7 in a CTAB (cetyltrimethylammonium bromide) containing buffer and the TMB substrate (3,3',5,5' tetramethylbenzidine enzyme-immunoassay (EIA)) in well 8 turned from a clear solution to a blue solution depending on if any peroxidase was carried via the dipstick into the well by binding to the amplification products. The plate containing the 8-well microwell strip was quantitatively read at 650 nm using a microwell plate reader.

The same samples were analyzed by this universal solid phase dipstick assay and by the bead dipstick assay described in Example 1, although the conjugate in well 5 of the bead assay was changed to anti-fluorescein-peroxidase because of the change in PCR primers. The bead assay results were quantitated with a reflectance based reader since the dye precipitated on the beads. In order to compare the dissimilar units in the two assay formats the color for the DQB1 specific test is divided by the DRA specific test. The following figure shows these results. The results (Table V) indicate that both formats perform equally well showing the expected sensitivity and specificity.

TABLE V

HLA ALLELE DETECTION ASSAY FORMAT COMPARISON

| FORMAT | RATIO DQB/DRA | | | RATIO DQB/DRA | | |
|---|---|---|---|---|---|---|
| | MICRO-WELL | MICRO-WELL | MICRO-WELL | BEAD | BEAD | BEAD |
| SPECIFICITY | 0201 | 0302 | 0602 | 0201 | 0302 | 0602 |
| 0201 | 0.40 | −0.01 | 0.02 | 0.38 | 0.02 | 0.01 |
| 0302 | 0.00 | 0.49 | −0.01 | 0.01 | 0.10 | 0.01 |
| 0602 | 0.01 | 0.00 | 0.18 | 0.01 | 0.01 | 0.15 |

All publications and patents mentioned in this specification are herein incorporated by reference into the specification to the same extent as if each individual publication or patent was specifically and individually indicated to be incorporated herein by reference.

What is claimed is:

1. A method of detecting the presence of HLA DQB1 alleles 0201/0202, 0302/0303, and 0602 in a human biological sample, comprising the steps:
    (a) contacting, under stringent conditions, an amplicon comprising a sequence from codon 23 through 41 of the human leukocyte antigen (HLA) DQB1 gene with at least three unique human leukocyte antigen (HLA) DQB1 allele-specific probes to form a hybridization complex, wherein:
        said amplicon is no more than 2000 base pairs in length and is amplified with at least two primers, wherein one of said two primers selectively hybridizes, under stringent conditions, to the same nucleic acid sequence of the HLA DQB1 allele as a primer having the sequence 5'-GGAGCGCGTGCGTCTTGTG-3' (SEQ ID NO:7);
        said HLA DQB1 allele-specific probes is between 15 and 200 nucleotides in length; and
        wherein each of said DQB1 allele-specific probes includes a nucleic acid segment of at least 15 contiguous nucleotides which selectively hybridizes under stringent conditions to the same nucleic acid sequence of the HLA DQB1 allele as an oligonucleotide selected from the group consisting of:
        for the 0201 and 0202 alleles,

5'-AAGAGATCGTGCGCTTCGACA-3'    (SEQ ID NO:2), for the 0302 and 0303 alleles

5'-AGGAGTACGCACGCTTCGACA-3'    (SEQ ID NO:4), for the 0602 allele

5'-GGAGTACGCGCGCTTCGAC-3'    (SEQ ID NO:6), and complementary sequences thereof, with the proviso that each of said allele-specific probes selectively hybridizes under the same stringent hybridization conditions; and
    (b) detecting said hybridization complexes as an indication of the presence of said HLA DQB1 alleles 0201/0202, 0302/0303, and 0602.

2. The method of claim 1, wherein said amplicon is no longer than 1000 base pairs in length.

3. The method of claim 1, wherein said nucleic acid segments selectively hybridize under stringent conditions to at least 18 contiguous bases of an oligonucleotide selected from the group consisting of: SEQ ID NO:2, SEQ ID NO:4, SEQ ID NO:6, and complementary sequences thereof.

4. The method of claim 1, wherein said amplicon is no longer than 700 base pairs in length.

5. The method of claim 1, wherein said nucleic acid segment is complementary to an oligonucleotide selected from the group consisting of SEQ ID NO:2, SEQ ID NO:4, SEQ ID NO:6, and complementary sequences thereof.

6. The method of claim 1, wherein said amplicon further comprises a sequence having any number of contiguous bases in the sequence from codon 22 to 41.

7. The method of claim 1, wherein said amplicon is generated using a primer having the sequence which selectively hybridizes, under stringent conditions, to the same nucleic acid sequence of the HLA DQB1 allele as a primer having the sequence 5'-TCTGGCTGTTCCAGTACTCGGC-3' (SEQ ID NO:8).

8. A method of detecting the presence of HLA DQB1 alleles 0201/0202, 0302/0303, and 0602 in a human biological sample, comprising the steps:

(a) contacting an amplicon comprising a sequence from codon 23 through 50 of the human leukocyte antigen (HLA) DQB1 gene with at least three unique human leukocyte antigen (HLA) DQB1 allele-specific probes to form a hybridization complex, wherein:

said amplicon is no more than 2000 base pairs in length and is amplified with at least two primers, wherein one of said two primers selectively hybridizes, under stringent conditions, to the same nucleic acid sequence of the HLA DQB1 allele as a primer having the sequence 5'-GGAGCGCGTGCGTCTTGTG-3' (SEQ ID NO:7);

said HLA DQB1 allele-specific probes is between 15 and 200 nucleotides in length; and wherein each of said DQB1 allele-specific probes includes a nucleic acid segment of at least contiguous nucleotides which selectively hybridizes under stringent conditions to the same nucleic acid sequence of the HLA DQB1 allele as an oligonucleotide selected from the group consisting of:

for the 0201 and 0202 alleles

| | |
|---|---|
| 5'-CGTGGGGGAGTTCCGGGCGGTG-3' | (SEQ ID NO:1), |
| 5'-AAGAGATCGTGCGCTTCGACA-3' | (SEQ ID NO:2), | for the 0302 and 0303 alleles

| | |
|---|---|
| 5'-CGTGGGGGTGTATCGGGCGGTG-3' | (SEQ ID NO:3), |
| 5'-AGGAGTACGCACGCTTCGACA-3' | (SEQ ID NQ:4), | for the 0602 allele

| | |
|---|---|
| 5'-CGTGGGGGTGTACCGCGCGGTG-3' | (SEQ ID NO:5), |
| 5'-GGAGTACGCGCGCTTCGAC-3' | (SEQ ID NO:6), | and complementary sequences thereof, with the proviso that each of said allele-specific probes selectively hybridizes under the same stringent hybridization conditions; and (b) detecting said hybridization complexes as an indication of the presence of said HLA DQB1 alleles 0201/0202, 0302/0303, and 0602.

9. The method of claim 8, wherein said amplicon is no longer than 1000 base pairs in length.

10. The method of claim 8, wherein said nucleic acid segments selectively hybridize under stringent conditions to at least 18 contiguous bases of an oligonucleotide selected from the group consisting of: SEQ ID NO:2, SEQ ID NO:4, SEQ ID NO:6, and complementary sequences thereof.

11. The method of claim 8, wherein said amplicon is no longer than 700 base pairs in length.

12. The method of claim 8, wherein said nucleic acid segment is complementary to an oligonucleotide selected from the group consisting of: SEQ ID NO:1, SEQ ID NO:2, SEQ ID NO:3, SEQ ID NO:4, SEQ ID NO:5, SEQ ID NO:6, and complementary sequences thereof.

13. The method of claim 8, wherein said amplicon further comprises a sequence having any number of contiguous bases in the sequence from codon 22 to 50.

14. The method of claim 8, wherein said amplicon is generated using a primer which selectively hybridizes, under stringent conditions, to the same nucleic acid sequence of the HLA DQB1 allele as a primer having the sequence 5'-TCTGGCTGTTCCAGTACTCGGC-3' (SEQ ID NO:8).

15. The method of claim 8, wherein said three unique probes have sequences shown in SEQ ID NO:1, 3, and 5, or SEQ ID NO:2, 4, and 6.

16. A kit for detecting the presence of HLA DQB1 alleles 0201/0202, 0302/0303, and 0602 in a human biological sample, comprising at least three probes of 15 to 100 nucleotides in length, said probes comprising a nucleic acid segment which is complementary to the same nucleic acid sequence of the HLA DQB1 allele as an oligonucleotide selected from the group consisting of: SEQ ID NO:1, SEQ ID NO:2, SEQ ID NO:3, SEQ ID NO:4, SEQ ID NO:5, SEQ ID NO:6, and complementary sequences thereof.

* * * * *

UNITED STATES PATENT AND TRADEMARK OFFICE
CERTIFICATE OF CORRECTION

PATENT NO. : 6,319,671 B1
DATED : November 20, 2001
INVENTOR(S) : U'ren et al.

It is certified that error appears in the above-identified patent and that said Letters Patent is hereby corrected as shown below:

<u>Column 21, claim 8,</u>
Lines 19-20, delete "at least contiguous" and substitute therefor, -- at least 15 contiguous --.

Signed and Sealed this

Nineteenth Day of March, 2002

Attest:

JAMES E. ROGAN
*Director of the United States Patent and Trademark Office*

*Attesting Officer*